United States Patent [19]

Bordoloi et al.

[11] Patent Number: 4,714,655
[45] Date of Patent: Dec. 22, 1987

[54] PRESSURE-SENSITIVE ADHESIVE CONTAINING HEAT-SENSITIVE MATERIALS, AND METHOD OF MAKING THE SAME

[75] Inventors: Binoy K. Bordoloi, Covina; Yehuda Ozari, Arcadia, both of Calif.; Gerald R. Dever, Mentor, Ohio

[73] Assignee: Avery International Corporation, Pasadena, Calif.

[21] Appl. No.: 784,521

[22] Filed: Oct. 4, 1985

[51] Int. Cl.[4] .............................................. B05D 3/06
[52] U.S. Cl. ...................................... 428/345; 427/2; 427/44; 427/54.1; 427/208.4; 428/355; 604/890; 604/896; 604/897
[58] Field of Search ................. 427/2, 44, 54.1, 208.4; 604/890, 896, 897; 428/345, 355

[56] References Cited

U.S. PATENT DOCUMENTS

| | | | |
|---|---|---|---|
| 2,241,384 | 5/1941 | Bateman et al. | 427/2 |
| 3,087,850 | 4/1963 | Cole | 427/208.4 |
| 3,457,919 | 7/1969 | Harbard | 427/2 |
| 3,632,740 | 1/1972 | Robinson et al. | 427/208.4 |
| 4,251,302 | 2/1981 | Leonard et al. | 427/208.4 |
| 4,310,509 | 1/1982 | Berglund et al. | 604/897 |
| 4,321,117 | 3/1982 | Kaetsu et al. | 604/890 |
| 4,460,369 | 7/1984 | Seymour et al. | 604/897 |
| 4,485,087 | 11/1984 | Otsuka et al. | 604/896 |

Primary Examiner—John H. Newsome
Attorney, Agent, or Firm—Christie, Parker & Hale

[57] ABSTRACT

A heat-sensitive material is incorporated into a fluid prepolymer precursor of a pressure-sensitive adhesive to form a stable mixture. The mixture is cast onto a substrate, and the prepolymer is polymerized into a pressure-sensitive adhesive by the action of ultraviolet radiation, electron-beam radiation, or a combination thereof.

26 Claims, 4 Drawing Figures

PRESSURE-SENSITIVE ADHESIVE CONTAINING HEAT-SENSITIVE MATERIALS, AND METHOD OF MAKING THE SAME

BACKGROUND OF THE INVENTION

The present invention is directed to pressure-sensitive-adhesive constructions containing releasable heat-sensitive materials, particularly to the methods for their production.

There are contained in the pressure-sensitive adhesive of the construction to which the invention relates, heat-sensitive materials which are volatile and/or temperature-sensitive. The pressure-sensitive-adhesive structure enables controlled release of the entrained materials. Materials to be included range from medicaments to fragrances to repellants.

Pressure-sensitive adhesives are normally formed by bulk, solvent or emulsion polymerization. In the application of such pressure-sensitive adhesives to a substrate, heat is required to achieve a useful product. In the case of a bulk adhesive, the adhesive is normally applied to a substrate by hot-melt techniques. In the case of a solvent-based pressure-sensitive adhesive, the adhesive layer is formed, after being cast onto a substrate, by evaporation of the solvent through application of heat. The same is true where the adhesive layer is cast as a coatable emulsion.

A definite body of art has aligned itself towards the controlled release of medicaments. This art is called "transdermal delivery systems." U.S. Pat. Nos. 3,598,123 and 3,731,683, both to Zaffaroni, disclose the use of reservoirs, such as microcapsules, as the agent to control the release of medicaments from a pressure-sensitive adhesive contained on a carrier such as a bandage.

U.S. Pat. No. 3,632,740 to Robinson et al discloses the inclusion of corticosteriods in pressure-sensitive adhesive bases.

U.S. Pat. No. 3,699,963, also to Zaffaroni, pertains to the controlled release of a drug to the oral mucosa, again through the use of microcapsules from a pressure-sensitive adhesive.

U.S. Pat. No. 4,073,291 to Marvel et al pertains to the inclusion of tretinoin in a pressure-sensitive adhesive for control of acne.

While U.S. Pat. No. 4,336,243 to Sanvordeker et al pertains to a silicone-matrix pad which contains, and which controls administration of, nitroglycerin, U.S. Pat. No. 4,421,732 to Komuro et al also pertains to a pressure-sensitive tape containing nitroglycerin, the adhesive being rubber-base and the nitroglycerin being dissolved therein.

Scopolamine is stored for delivery in one construction consisting of four layers. To an impervious bonding layer there are added, in sequence, a drug reservoir of scopolamine, mineral oil, and polyisobutylene; a microporous polypropylene membrane which controls the rate of delivery of scopolamine; and, finally, an adhesive layer of mineral oil, polyisobutylene and scopolamine. After removal of a peel strip, the adhesive is applied to the skin behind the ear, and protects against motion sickness for up to three days.

Other than by the use of the microspheres or membranes, or perhaps concentration of the contained agent, means to modify the system for control of the release of the contained agent from the adhesive, are not disclosed in this body of art.

The present invention is directed to curing the deficiencies of the prior art, to provide a broad-based system for enabling controlled release of agents contained in adhesives and related strips, particularly to the retention and controlled release of thermally-sensitive materials, i.e., materials which have a relatively low vapor pressure and which would be lost upon application of heat, or would undergo undesirable thermal alteration by application of heat.

SUMMARY OF THE INVENTION

According to the present invention there is provided a system which enables controlled release of a heat-sensitive material which could not be contained in a pressure-sensitive adhesive and which would be lost or destroyed by conventional methods of forming a pressure-sensitive adhesive on the surface of a carrier.

In accordance with the instant invention, therefore, there is applied directly to the surface of a web, either a carrier web or a web for transfer on an adhesive to a carrier web, a fluid system having a viscosity sufficient to be coated onto the surface and comprising a predetermined amount of at least one thermally-sensitive material, and a prepolymer which, when subjected to the action of ultraviolet and/or electron-beam radiation, is polymerized, i.e., chain-extended and/or crosslinked, at a temperature below the volatilization temperature of the contained material or the thermal degradation temperature of the contained material, so as to form a pressure-sensitive-adhesive product in which the material to be released is contained in a matrix of the formed pressure-sensitive adhesive. Chain extension and/or crosslinking control release of the heat-sensitive material, with the rate of release also being controlled by concentration of the contained heat-sensitive material. By use of the method disclosed, releasable materials of relatively high concentration can be retained without loss of pressure-sensitive properties of the polymerized mass.

DETAILED DESCRIPTION

According to the present invention there is provided a process for the production of pressure-sensitive adhesive stock containing volatile and/or transmittable heat-sensitive materials whose rate of release from the pressure-sensitive-adhesive surface is controlled by the polymerization of such surface by ultraviolet (UV) radiation, electron-beam (EB) radiation, or a combination thereof. By the term "polymerization" as used herein, there is meant chain extension, crosslinking, or a combination of the two. The term "heat-sensitive" as used herein applies to materials which have a vapor pressure sufficiently low to be considered volatile, or which undergo adverse chemical changes upon application of heat.

The invention comprises, in combination, applying to a substrate, a layer of fluid composition containing a controlled amount of heat-sensitive material and prepolymer, and converting the prepolymer into a pressure-sensitive adhesive, substantially without a significant rise in temperature, by exposing the prepolymer containing the heat-sensitive material to the action of UV radiation, EB radiation, or any combination of the two. When combined, UV radiation followed by EB radiation is presently preferred. Exposure is for a time sufficient to form, by polymerization, a pressure-sensitive adhesive, substantially without loss of the heat-sensitive material by vaporization or degradation. The pressure-sensitive adhesive may be formed on a low-energy-release surface, normally a silicone release surface, and transferred to a carrier substrate; formed directly on a carrier substrate; or formed while contained inbetween a laminate of a substrate having a low-energy-release surface (release liner) and a carrier substrate.

Figure 1A:
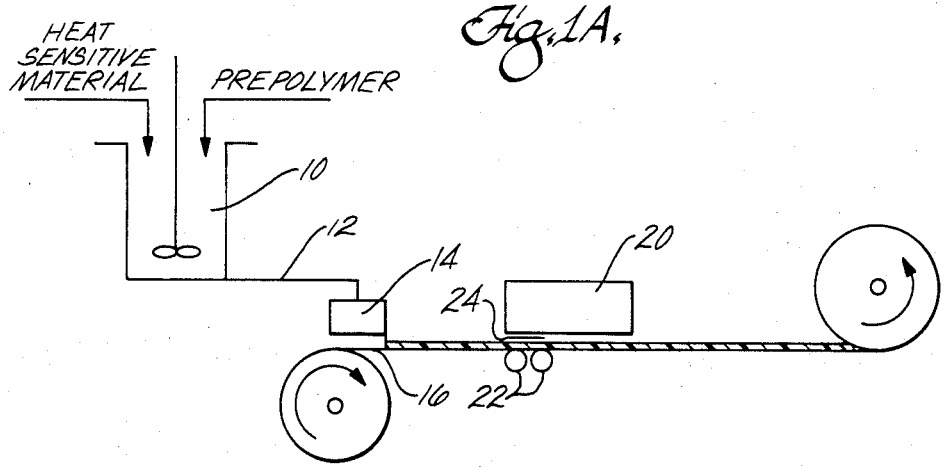
FIG. 1A, 1B, and 1C schematically illustrate methods for carrying out the process of the instant invention.
Figure 1B:
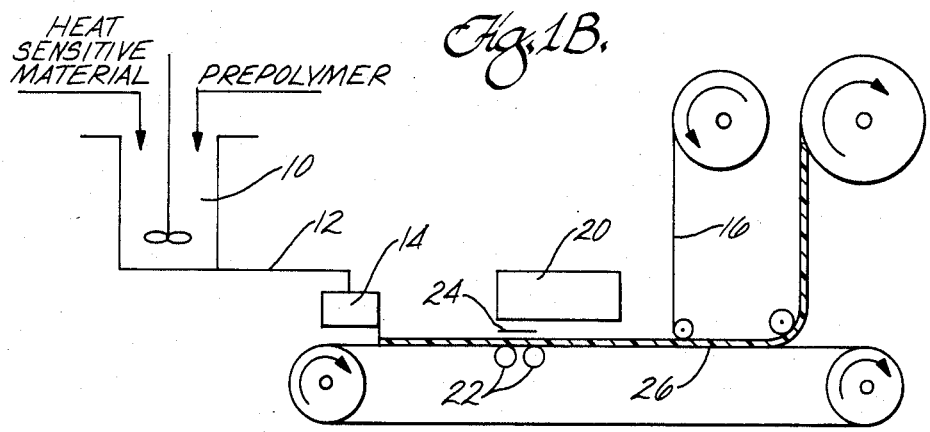
Figure 1C:
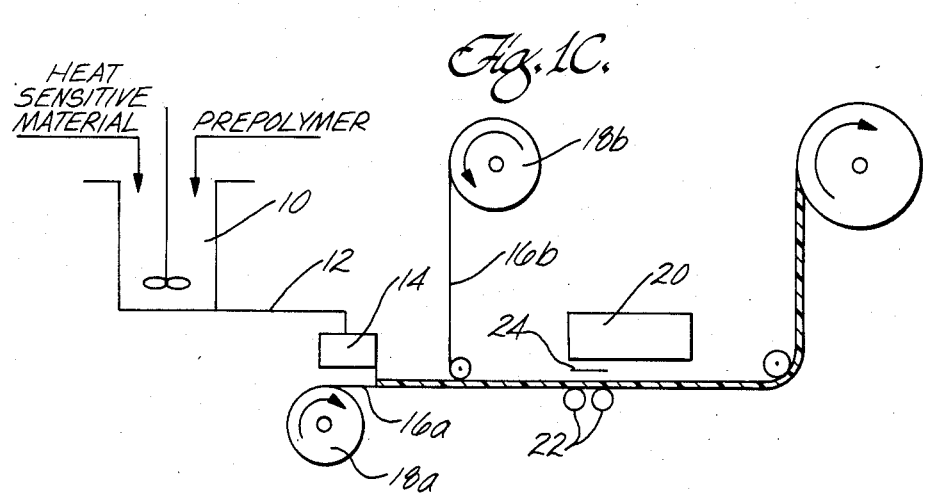

With reference now to FIG. 1A, 1B, and 1C, there are illustrated means by which to carry out the practice of the instant invention. In each embodiment, a prepolymer is mixed in mixing tank 10 with the heat-sensitive material to be retained therein, and transferred by line 12 to coater 14, where, by conventional techniques, it is applied directly to carrier substrate 16, which is dispensed from roll 18. The web is coated to a predetermined thickness and passed to a radiation source 20, which may be UV, EB, or a combination of the two. Polymerization is to a level sufficient to provide a final product having a pressure-sensitive-adhesive surface which contains a heat-sensitive material that is released with time.

Where UV polymerization is employed, some exotherm may develop from polymerization, and may be removed using chill rolls 22. A unique feature of the instant invention, however, is that, by applying the prepolymer as a thin film to the surface of the carrier web, any heat generated will be quickly dissipated, with little or no temperature rise and consequent little loss of vaporization and/or deleterious degradation of the heat-sensitive material. For most materials, it is desired to keep the temperature below about of 150° C. or less. As an additional means of heat control, where UV lamps are employed, is to intersperse a heat filter 24 between the UV lamps and the fluid surface to be polymerized to a pressure-sensitive adhesive.

As illustrated in FIG. 1B, the fluid composition is applied to an endless web 26 of a low-energy-release surface and transferred, after polymerization, to the carrier web or substrate 16.

In the alternative, as shown in FIG. 1C, the coating is applied to either carrier web or substrate 16a or to a low-energy-release-surface substrate or protective release liner 16b, fed from rolls 18a or 18b, and the combination is passed under the radiation source to enable polymerization, to form the pressure-sensitive adhesive.

As used herein, by the term "prepolymer" there is meant systems containing reactants which are polymerizable by chain extension and/or crosslinking and which range from monomers to oligomers to "A-stage" resins and combinations thereof, and which are liquid in a temperature range of from ambient to the temperature at which the heat-sensitive material to be contained by a pressure-sensitive adhesive formed therefrom, will volatilize or thermally degrade. For normal applications it is desired to keep the temperature below 150° C., and preferably about ambient temperature.

Among the useful prepolymers are monomers, oligomers, low-molecular-weight polymers formed of monomers and/or oligomers such as acrylates, methacrylates, acrylated urethanes, acrylated epoxies, acrylated acrylics, methacrylated urethanes, methacrylated epoxies, methacrylated acrylics, unsaturated carboxylic acids, rubber-based monomers, and the like. Acrylic-based prepolymers are presently preferred.

Without being limited, the following are monomers which may be employed in the practice of the instant invention. They include ethyl acrylate, butyl acrylate, 2-ethylhexyl acrylate, butylacrylate, isooctylacrylate, $\beta$-carboxyethyl acrylate, ethoxy carboxyethyl acrylate, maleic anhydride, monoethylitaconate, polyoxyethylene acrylate, dibutyl fumarate, vinyl pyrrolidone, tetraethyleneglycol acrylate, vinyl acetate, acrylic acid, methacrylic acid, itaconic acid, styrene, butadiene, isoprene, and the like.

Multifunctional monomers can be effectively used to enhance crosslinking, creating a lattice containing the heat-sensitive material.

"Multifunctional monomers" as used herein means monomers having 2 or more pendant functional groups. Illustrative multifunctional monomers include pentaerythritol triacrylate (PETA), triethyleneglycol diacrylate, triethyleneglycol dimethacrylate, trimethylol propane trimethacrylate, trimethylol propane triacrylate, tripropyleneglycol diacrylate, tripropyleneglycol dimethacrylate, 1,3-butyleneglycol dimethacrylate, tetraethyleneglycol dimethacrylate, and the like. Concentration of multi-functional monomers may be up to about 8% by weight, more preferably from about 1% to about 5% by weight, based on the total weight of the prepolymer, which lowers the energy required to achieve a given level of crosslinking.

The prepolymer is generally formed to a coating viscosity of from about 0.3 P.s (Pascal-second) or less, to about 1,000 P.s or more. It may be coated on the surface by reverse rolls, gravure printing, meyer bar, slot- or die-coating, extrusion coating, and the like. Fillers and thixotropic agents may be employed to enhance integrity of the fluid coating on the surface until polymerization occurs. Coating thickness is generally from about 0.2 to about 0.5 mm, with greater heat problems existing for thicker coating.

As indicated, polymerization can be open-faced, e.g., polymerization can occur in air if the air does not retard reaction or adversely affect the reaction, or it can occur in a substantially inert atmosphere.

Polymerization may be closed-faced, e.g., the fluid may be contained between a carrier substrate and a release liner, with polymerization being perfected while the two are laminated to the liquid core. A combination of the two procedures may also be employed.

In the practice of the instant invention, whether one employs EB or UV radiation, or a combination thereof, will depend primarily on the type of reactions to be achieved. Ultraviolet radiation is particularly beneficial to achieve chain extension and/or crosslinking polymerization, and requires the use of a photoinitiator. Benzophenone is presently preferred. Other initiators include 2,2-diethoxyacetophenone (DEAP) and 2,2-dimethoxy-2-phenyl acetophenone (Irgacure TM 651), and the like. Concentration may range from about 0.1% to about 3% by weight of the prepolymer. UV polymerization occurs with an exotherm. However, in most instances, the exotherm has no consequential effect, since polymerization occurs within a thin surface, and any temperature rise is rapidly dissipated. Where there is an accumulation of heat because of the thickness of the layers or the construction employed, chill rolls may be used to remove the heat of reaction, thereby maintaining the system at a practical temperature.

If the prepolymer is of sufficient molecular weight, albeit not yet a pressure-sensitive adhesive, EB polymerization can be utilized to induce pressure-sensitive-adhesive properties, namely, converting the liquid composition to an inherently tacky material having a glass-transition temperature of less than about $-20°$ C., preferably less than about $-25°$ C., and normally at least 40° C. below the use-temperature. However, where chain extension is desired in combination with crosslinking, the coated prepolymer and additive are normally subjected to UV radiation for chain extension, followed by EB radiation to achieve crosslinking. Levels of EB radiation which can be effectively employed, range from about 10 to about 100 kiloGray (kGy).

In the practice of the instant invention there is retained a heat-sensitive material in a pressure-sensitive-adhesive matrix formed by UV and/or EB radiation, the rate of release of which can be controlled by the degree of crosslinking employed. All that is required for the precursor of the pressure-sensitive adhesive is that it be coatable on at least a carrier substrate or web; that it yield, upon exposure to the radiation employed, a pressure-sensitive adhesive capable of retaining the releasable material to be incorporated within the adhesive; and that it be able to undergo polymerization to a temperature at which volatilization of the retained material will occur, or at which thermal degradation of the retaining material will occur. In addition, the precursors must not react with the retained heat-sensitive material to render it immobile. The retained heat-sensitive material can vary widely. It may range from a medicament to a fragrance to a repellent and the like. The functionality of the retained heat-sensitive material is determined by release from the pressure-sensitive-adhesive matrix at a controlled rate, of ointments containing, for example, menthol, methyl salicylate, methyl salicylate/-menthol blends, scopolamine and nitroglycerin, which penetrate the skin, to materials which enhance acceptance of an individual, such as a fragrance, or materials which enhance the comfort of an individual, such as a muscle painkiller or an insect repellant.

The nature of the adhesive and the carrier web employed will depend upon the application. For instance, where the end-product is small, such as in medical applications, there may be employed impervious webs which insure that the medicament will be released only to the skin, as opposed to being vaporized through the carrier web. Where, however, the area covered by the carrier web is large, the web employed may be made porous in order to transmit moisture, so as to prevent skin masturation over the period of time during which the medicament is being absorbed by, or is in contact with, the skin. This may result in some loss of the medicament employed, which is a small sacrifice in terms of patient comfort.

For such applications, the adhesive and any initiator employed are those which will be accepted by the food and drug agencies as being generally regarded as safe for human use. In this regard, EB radiation has been found to be very effective in causing polymerization of any residual monomers or oligomers which may be present in the liquid polymer system applied to the web for polymerization, to the end that there will be essentially no skin irritation due to unreacted monomers.

In the case of release of fragrances or repellants, the adhesive can be advantageously formulated to preferentially adhere to a cloth substrate, such that the fragrance or repellant is not directly in contact with the skin but is emitted through the surface of a cloth, say when adhered to the interior of a jacket or the like. In this application, the web may also contain the fragrance or repellant to be employed so that both are advantageously used for controlled release of the fragrance or the repellant. Where the carrier web of the adhesive is adhered to the interior of a cloth surface which would otherwise be in contact with the skin, however, isolation of the skin from the material to be released can be advantageously realized by using a web free of the heat-sensitive material to be released and free of any skin irritant.

There may be included in the prepolymer other materials which are heat-sensitive such as fillers, tackifiers, colorants, anti-oxidants, and the like, the functionality of which is old in the adhesive art.

While nowise limiting, the following is illustrative of the instant invention.

EXAMPLE 1

To include a liquid medicament combination of menthol (M) and methyl salicylate (MS) in a ratio of 2:3 at a loading up to about 25% into a room-temperature, coatable and curable pressure-sensitive adhesive, there was used a prepolymer known as Acronal DS-3293, made and supplied by BASF. The prepolymer had a viscosity, at 22° C. and 2-per-sec. shear rate, of about 180 P.s. Analysis revealed it to be a copolymer (oligomer) comprising 2-ethylhexyl acrylate, vinyl acetate, and acrylic acid, in admixture with alcohols containing 8 or more carbon atoms. The low-molecular-weight component, with both acrylic unsaturations and hydroxyl functionality, was compatible with methyl salicylate and menthol. Due to low-melt elasticity, this material was readily coated between two squeeze rolls (bull-nose) at room temperature and was converted into a pressure-sensitive adhesive under electron-beam radiation (EB) without added crosslinking agents at as low a dosage as 10 kGy. Some standard peel-tack-shear data for a Mylar substrate web on stainless steel panels, at a coating weight of 50 g/m$^2$, are shown in Table I.

TABLE I

| EB Dosage/kGy | 10 | 30 | 50 | 70 |
|---|---|---|---|---|
| RTS 1000 g (ks) | 2.3 | 4.8 | 3.8 | 5.7 |
| 180° Peel (N/m) | 324 | 352 | 360 | 342 |
| Loop Tack (N/m) | 290 | 300 | 360 | 384 |
| Polyken Tack (kPa) | 228 | 198 | 191 | 212 |

RTS = Room-Temperature Shear, ASTM D-3654-78, PSTC #7-6th Ed., ASTM D-1000-68
180° Peel = PSTC-1-6th. Ed., PLMI-VII Ld-4-68
ks = kiloseconds
N/m = Newtons per meter
kPa = kiloPascal, Newtons per square meter
Loop Tack = PSTC #5-6th Ed.
Polyken Tack = ASTM D-2979-71 using A-1-1 probe

EXAMPLE 2

As indicated herein, electron-beam irradiation primarily gave rise to cross linking and very little chain extension. This result is indicated by the low peel values. It was hypothesized that the peel adhesion could be improved by chain extension, by ultraviolet curing-/polymerization prior to crosslinking by electron beam. Therefore, 1% by weight of a UV initiator (DEAP) was added to the mixture of the prepolymer and the medicament combination. These samples were UV polymerized using two 200 watt/inch UV lamps at varying speeds; the higher the speed of the web, the lower the dose from UV. They were then EB polymerized. Some heat was generated in UV polymerization, but a negligible amount during EB polymerization.

The liquid ingredients (M/MS) were loaded in the prepolymer at both 10% and 25% by weight based on the weight of the medical ingredients and the prepolymer, and were coated at 100 g/m² on Supertuf ™ release liner at room temperature. These were polymerized open-face, under conditions of EB only, UV only, and UV followed by EB polymerization.

The data on 180° peel on glass are summarized in Table II. The weight ratio of the medicament combination (M:MS) was 2:3. Only panel mode of failure was observed, even when the loading was 25% M/MS. As in Example 1, coating weight was 100 g/m². The following observations were made:

(a) At both 10% and 25% loading, peel was the lowest at only EB curing, and the higher the loading of M/MS, the lower the peel;

(b) The UV polymerization alone, without any EB polymerization, gave a "stringy", poorly polymerized material, at least at high loading of M/MS. Thiss result was attributed to a lack of adequate cross-linking;

(c) UV polymerization followed by EB polymerization, gave improved peel. The more the UV radiation (lower speeds) received by the material prior to EB, the higher the peel. The higher the loading of M/MS, the lower the peel; and (d) Any peel value in the range of from 100 to 600 N/m (panel), could be generated by combined ambient temperature coating and UV-EB polymerization.

TABLE II (Mylar/Glass Panel)

| Treatment or Property | Value | | | |
|---|---|---|---|---|
| M/MS 10% BY WEIGHT | | | | |
| UV (ft/min) | 15 | 20 | 30 | None |
| EB (kGy) | 30 | 30 | 30 | 30 |
| 180° Peel (N/m) | 350 ± 49 | 315 ± 0 | 254 ± 12 | 140 ± 0 |
| M/MS 25% BY WEIGHT | | | | |
| UV (ft/min) | 2x @ 15 | 10* | 15* | None |
| EB (kGy) | 30 | 30 | 30 | 30 |
| 180° Peel (N/m) | 613 | 219 | 105 | 44 |

*When only UV polymerized, whether at 10 or 15 ft/min, and not followed by any EB polymerization, the material remained too "stringy", and did not cure well. Therefore, it could not be tested for 180° peel.

EXAMPLE 3 AND CONTROL

As a Control there was used "Salonpas", a product manufactured by Hisamitsu Pharmaceutical Co. of Japan, which product was determined to contain, on a 250 cm² basis, the following ingredients:

| methyl salicylate | 330 mg |
|---|---|
| l-menthol | 300 mg |
| dl-camphor | 65 mg |
| glycol salicylate | 50 mg |
| thymol | 42 mg |
| tocophenol acetate | 6 mg |

Figure 2:
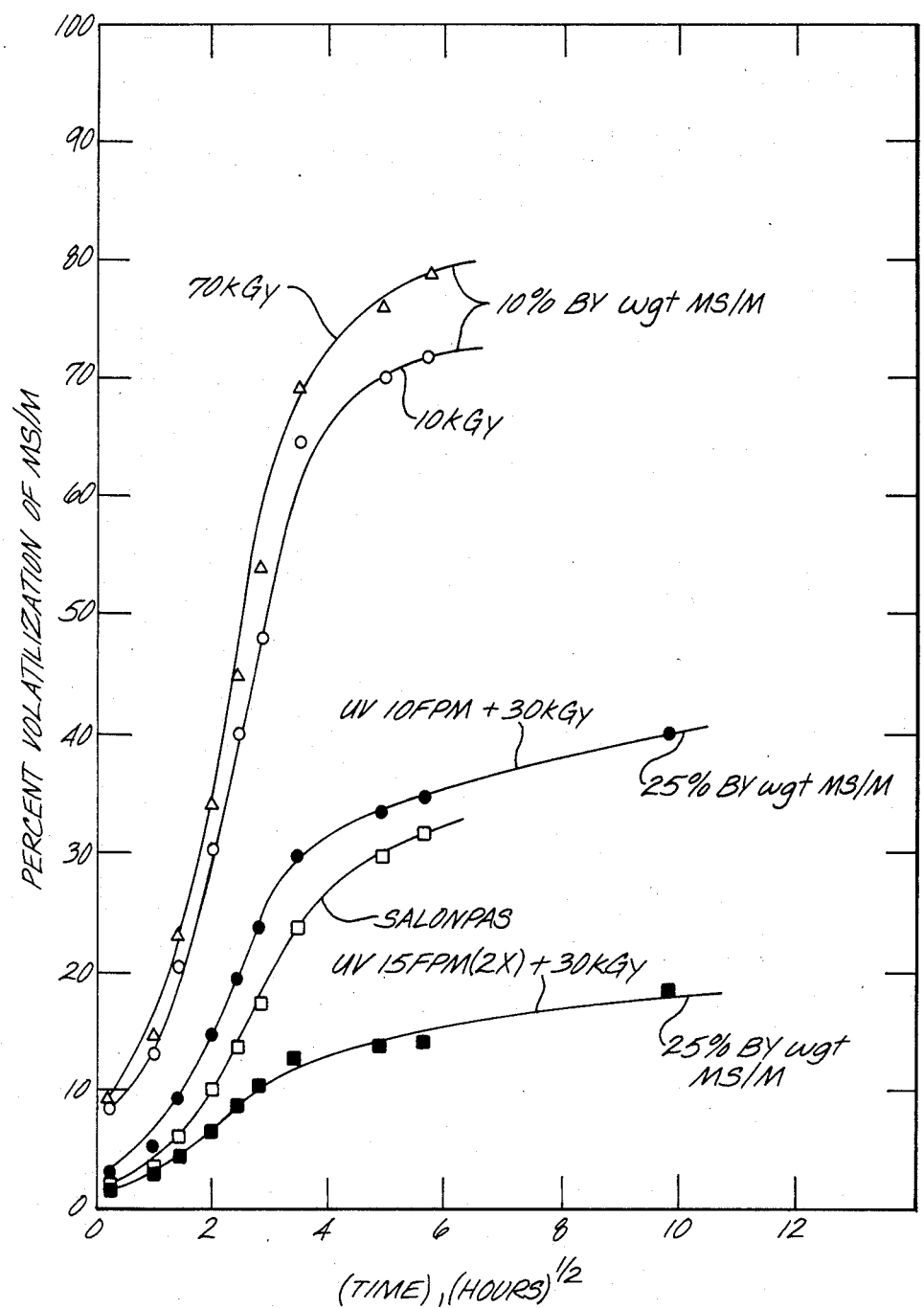
FIG. 2 illustrates volatilization of a mixture of methyl salicylate and menthol in a weight proportion of 3:2 from a pressure-sensitive surface formed in the presence of the medicament by electron-beam (EB) radiation, or by ultraviolet (UV) radiation followed by electron-beam radiation, as against another product containing the same volatile materials.

The facestock is a flesh-colored cellulosic fabric, which is about 8–9 mils thick. The adhesive is about 6–7 mils thick and is a rubber-based adhesive similar to "rubber cement." The adhesive is highly filled with about 30 weight-percent calcium carbonate/metal oxides such as zinc oxide. A tackifier component of the adhesive is similar to a rosin-modified phenolic resin. The release liner is a corrugated, clear polypropylene film with no detectable release coating. The amount of active ingredients incorporated into the adhesive layer calculated out to about 19–20 weight-percent. The "Salonpas" product has very low conventional adhesive properties but sticks very well to the skin. Release of the content of this product against those prepared in accordance with Examples 1 and 2 of the instant invention, and residual adhesive properties, are shown in FIG. 2 and Table III. As compared to "Salonpas," the composition of the instant invention had higher initial and residual adhesive properties and, with reference to FIG. 2, demonstrate the ability to use EB, and UV plus EB, to modify the rate of release from the polymerized Acronal DS-3293.

TABLE III

| Process Condition | 180° Peel Adhesion (N/m) on on Stainless Steel | | Polyken Tack (kPa) | |
|---|---|---|---|---|
| | Before* | After* | Before* | After* |
| M/MS 10% BY WEIGHT (2.8 mils) | | | | |
| EB Only | | | | |
| 10 kGy | 87.5 | 350 | 340 | 500 |
| 30 kGy | 122.5 | 385 | 440 | 475 |
| 50 kGy | 157.5 | 402.5 | 435 | 425 |
| 70 kGy | 175 | 420 | 870 | 820 |
| M/MS 25% BY WEIGHT (2.5 mils) | | | | |
| UV + EB | | | | |
| 10 fpm + 30 kGy | 245 | 507.5 | 465 | 495 |
| 15 fpm + 30 kGy | 210 | 542.5 | 485 | 400 |
| 15 fpm(2x) + kGy | 490 | 577.5 | 535 | 400 |
| "SALONPAS" | | | | |
| | 35 | 87.5 | 25 | 25 |

*Before and after volatilization.

What is claimed is:

1. A process for the production of a pressure-sensitive-adhesive stock containing a heat-sensitive material which comprises:

(a) forming a mixture of a select amount of at least one heat-sensitive material in a fluid prepolymer, said mixture having a viscosity sufficient to enable casting of the mixture onto a substrate, said prepolymer being polymerizable when subjected to the action of ultraviolet radiation, electron-beam radiation, or a combination thereof, and substantially non-deleteriously reactive with said heat-sensitive material;

(b) casting said mixture onto a substrate; and (c) exposing said cast mixture to the radiant action of ultraviolet radiation, electron-beam radiation, or a combination thereof, for a time sufficient to convert said prepolymer into a pressure-sensitive adhesive containing a releasable amount of said heat-sensitive material.

2. A process as claimed in claim 1 in which the substrate is a carrier web for the pressure-sensitive adhesive.

3. A process as claimed in claim 1 in which the substrate is a transfer web for the pressure-sensitive adhesive and in which the process includes the step of transferring the formed pressure-sensitive adhesive containing the heat-sensitive material, to a carrier web for the pressure-sensitive adhesive.

4. A process as claimed in claim 1 in which the fluid mixture of prepolymer and heat-sensitive material are contained between a carrier web for the pressure-sensitive adhesive and a release liner, when subject to the radiant action.

5. A process as claimed in claim 1 in which the heat-sensitive material is volatile.

6. A process as claimed in claim 1 in which the heat-sensitive material is thermally degradable.

7. A process as claimed in claim 1 in which the heat-sensitive material is volatile and in which the prepolymer is substantially converted to a pressure-sensitive adhesive without a deleterious increase in the temperature of said prepolymer.

8. A process as claimed in claim 1 in which the heat-sensitive material is thermally degradable and in which the prepolymer is converted into a pressure-sensitive adhesive at a temperature below the thermal degradation temperature of the heat-sensitive material.

9. A process for the production of a pressure-sensitive-adhesive stock containing a heat-sensitive material which comprises:
   (a) forming a mixture of a select amount of at least one heat-sensitive material in a fluid prepolymer comprising at least one acrylate monomer, said mixture having a viscosity sufficient to enable casting of the mixture onto a substrate, said prepolymer being polymerizable when subjected to the action of ultraviolet radiation, electron-beam radiation, or ultraviolet radiation followed by electron-beam radiation, and substantially non-reactive with said heat-sensitive material;
   (b) casting said mixture onto a substrate; and
   (c) exposing said cast mixture to the radiant action of ultraviolet radiation, electron-beam radiation, or ultraviolet radiation followed by electron-beam radiation, for a time sufficient to convert said prepolymer into a pressure-sensitive adhesive containing a releasable amount of said heat-sensitive material.

10. A process as claimed in claim 9 in which the substrate is a carrier web for the pressure-sensitive adhesive.

11. A process as claimed in claim 9 in which the substrate is a transfer web for the pressure-sensitive adhesive and in which the process includes the step of transferring the formed pressure-sensitive adhesive containing the heat-sensitive material, to a carrier web for the pressure-sensitive adhesive.

12. A process as claimed in claim 9 in which the fluid mixture of prepolymer and heat-sensitive material are contained between a carrier web for the pressure-sensitive adhesive and a release liner, when subject to the radiant action.

13. A process as claimed in claim 9 in which the heat-sensitive material is volatile.

14. A process as claimed in claim 9 in which the heat-sensitive material is thermally degradable.

15. A process as claimed in claim 9 in which the heat-sensitive material is volatile and in which the prepolymer is substantially converted to a pressure-sensitive adhesive without a deleterious increase in the temperature of said prepolymer.

16. A process as claimed in claim 9 in which the heat-sensitive material is thermally degradable and in which the prepolymer is converted into a pressure-sensitive adhesive at a temperature below the thermal degradation temperature of the heat-sensitive material.

17. A process as claimed in claim 13 in which the heat-sensitive material is selected from menthol, methyl salicylate, and blends of menthol and methyl salicylate.

18. A process as claimed in claim 17 in which the heat-sensitive material is a blend of menthol and methyl salicylate, and the weight ratio of menthol to methyl salicylate is about 2 to 3, and in which the blend is present in the pressure-sensitive adhesive in a concentration of from about 10 percent to about 25 percent by weight, based on the weight of the mixture.

19. A process as claimed in claim 18 in which the prepolymer comprises an oligomer of 2-ethylhexyl acrylate, vinyl acetate, and acrylic acid, in admixture with alcohols containing at least about 8 carbon atoms.

20. A process as claimed in claim 19 in which the mixture is subjected to ultraviolet radiation followed by electron-beam radiation.

21. A process as claimed in claim 15 in which the heat-sensitive material is selected from menthol, methyl salicylate, and blends of menthol and methyl salicylate.

22. A process as claimed in claim 21 in which the heat-sensitive material is a blend of menthol and methyl salicylate, and the weight ratio of menthol to methyl salicylate is about 2 to 3, and in which the blend is present in the pressure-sensitive adhesive in a concentration of from about 10 percent to about 25 percent by weight, based on the weight of the mixture.

23. A pressure-sensitive-adhesive stock comprising a face material and a pressure-sensitive adhesive containing a heat-sensitive material, said pressure-sensitive adhesive being formed by polymerizing a thin layer of a mixture of at least one heat-sensitive material in a fluid prepolymer onto a substrate, and exposing the mixture to the action of ultraviolet radiation, electron-beam radiation, or a combination thereof, for a time sufficient to convert the fluid prepolymer into a pressure-sensitive adhesive containing a releasable amount of the heat-sensitive material.

24. A pressure-sensitive-adhesive stock as claimed in claim 23 in which the heat-sensitive material is volatile.

25. A pressure-sensitive-adhesive stock as claimed in claim 24 in which the heat-sensitive material is menthol, methyl salicylate, or a mixture thereof.

26. A pressure-sensitive-adhesive stock as claimed in claim 25 in which the heat-sensitive material is a blend of menthol and methyl salicylate, and in which the weight ratio of menthol to methyl salicylate is about 2 to 3, and in which the blend is present in the pressure-sensitive adhesive in a concentration of from about 10 percent to about 20 percent by weight, based on the weight of the mixture.

* * * * *